United States Patent

Basko et al.

[11] Patent Number: 5,861,627
[45] Date of Patent: Jan. 19, 1999

[54] IMAGE RECONSTRUCTION FOR COMPTON CAMERA INCLUDING SPHERICAL HARMONICS

[75] Inventors: Roman Basko; Gengsheng Lawrence Zeng; Grant T. Gullberg, all of Salt Lake City, Utah

[73] Assignee: The University of Utah, Salt Lake City, Utah

[21] Appl. No.: 881,752

[22] Filed: Jun. 24, 1997

[51] Int. Cl.[6] .................................................. G01T 1/17
[52] U.S. Cl. ........................................... 250/363.04
[58] Field of Search ...................................... 250/363.04

[56] References Cited

U.S. PATENT DOCUMENTS

| | | |
|---|---|---|
| 4,055,765 | 10/1977 | Gerber et al. . |
| 4,185,274 | 1/1980 | Giallorenzi . |
| 4,437,007 | 3/1984 | Koslow et al. . |
| 4,529,882 | 7/1985 | Lee ........................................ 250/363.1 |
| 4,642,464 | 2/1987 | Mullani . |
| 4,833,327 | 5/1989 | Hart ...................................... 250/363.01 |
| 4,850,002 | 7/1989 | Harding et al. . |
| 4,857,723 | 8/1989 | Modisette . |
| 4,857,737 | 8/1989 | Kamae et al. . |
| 5,005,195 | 4/1991 | Lanza et al. . |
| 5,175,434 | 12/1992 | Engdahl . |
| 5,281,821 | 1/1994 | Antich et al. . |
| 5,334,849 | 8/1994 | Anderson et al. . |
| 5,457,321 | 10/1995 | Ichihara et al. ..................... 250/363.04 |
| 5,567,944 | 10/1996 | Rohe et al. .......................... 250/370.09 |
| 5,665,971 | 9/1997 | Chen et al. ........................... 250/385.1 |
| 5,742,056 | 4/1998 | Valentino et al. ................... 250/363.03 |

OTHER PUBLICATIONS

*Monte Carlo Study of a High Resolution Gamma Ray Telescope Used as a Polarimeter*, J. Park, et al., Workshop on High Resolution Gamma Ray Cosmology, UCLA, Nov. 2–3, 1988, © Elsevier Science Publishers B.V.

*Towards Direct Reconstruction from a Gamma Camera Based on Compton Scattering*, Michael J. Cree and Philip J. Bones, IEEE; Transactions on Medical Imaging; vol. 13, No. 2, Jun. 1994 IEEE.

*Primary Examiner*—Constantine Hannaher
*Attorney, Agent, or Firm*—Fay, Sharpe, Beall, Fagan, Minnich & McKee

[57] ABSTRACT

A diagnostic imaging system includes a Compton camera (14) disposed on a gantry (16). The camera (14) includes linear detectors (30$a$, 30$b$) for detecting radiation emanating from a subject to be imaged. A data processor (32) collects and processes radiation data in accordance with the detected radiation. Position and energy resolving circuitry (34) determines positions and energy deposited by photons striking the detectors. A cone projection generator (40) generates cone projection data or cone integrals based on the collected data which determine a possible location of a gamma source of the detected radiation. A conversion processor (41) converts the cone projection data into plane projection data. The conversion processor (41) includes a line integral processor (42) which determines line integrals representing the cone projection data and applies a spherical harmonic expansion to the line integrals. A plane integral generator (43) generates plane integrals such as Radon projection planes based on the line integrals. A reconstruction processor (44) reconstructs an image representation of a region of interest from the subject from the plane projection data using filtered back projection.

20 Claims, 5 Drawing Sheets ns. 5,861,627

IMAGE RECONSTRUCTION FOR COMPTON CAMERA INCLUDING SPHERICAL HARMONICS

BACKGROUND OF THE INVENTION

The present invention relates to the art of diagnostic imaging. It finds particular application in conjunction with nuclear or gamma cameras and will be described with particular reference thereto. It is to be appreciated, however, that the present invention will also find application in other non-invasive investigation techniques and imaging systems such as single photon planar imaging, whole body nuclear scans, positron emission tomography (PET), digital x-ray computed tomography and other diagnostic modes. It is to be further appreciated that the present invention will also find application in other Compton-based systems such as Compton-type telescopes used for astronomy.

Single photon emission computed tomography (SPECT) has been used to study a radionuclide distribution in a subject. Typically, one or more radiopharmaceuticals or radioisotopes are injected into a patient subject. The radioisotope preferably travels to an organ of interest whose image is to be produced. The patient is placed in an examination region of the SPECT system surrounded by large area planar radiation detectors. Radiation emitted from the patient is detected by the radiation detectors. The detectors have a mechanical collimator to limit the detector to seeing radiation from a single selected trajectory or ray, often the ray normal to the detector plane.

Typically, the detector includes a scintillation crystal that is viewed by an array of photomultiplier tubes. The relative outputs of the photomultiplier tubes are processed and corrected, as is conventional in the art, to generate an output signal indicative of (1) a position coordinate on the detector head at which each radiation event is received, and (2) an energy of each event. The energy is used to differentiate between emission and transmission radiation and between multiple emission radiation sources and to eliminate stray and secondary emission radiation. A two-dimensional projection image representation is defined by the number of radiation events received at each coordinate.

The mechanical collimator used in conventional gamma cameras, such as an Anger camera, localize the gamma emitters. This type of collimator, however, leads to low efficiency because only a fraction of the radiation passes through the collimator. Furthermore at any given time, only one view of an object of interest is obtained. Thus, the camera needs to move or rotate relative to a subject in order to collect all the data necessary for image reconstruction. Further, the collimators are fabricated of lead. Typically, each collimator is of sufficient weight that it must be connected to and removed from the head by mechanical, rather than human means. Not only is handling inconvenient, but the supporting structure for the detectors must support the detector head and hundreds of kilograms of collimator stably and without vibration.

A new type of gamma camera for SPECT relies on Compton scattering for gamma source localization and is known as a Compton camera. This camera has been proposed as an alternative to the conventional Anger camera and is advantageous because it uses electronic rather than mechanical collimation. Electronic collimation provides both high geometric efficiency and multiple image views. A proposed example of image reconstruction from data collected by a Compton camera is described in "Towards direct reconstruction from a gamma camera base on Compton scattering," by M. J. Cree and P. J. Bones, IEEE Trans. Med. Imag., Vol. 13, pp. 398–407, 1994. Although some progress has been made toward image reconstruction from a Compton camera system, at present, an acceptable filtered backprojection algorithm has proved elusive.

The present invention provides a new and improved reconstruction algorithm for a Compton camera which overcomes the above-referenced problems and others.

SUMMARY OF THE INVENTION

In accordance with the present invention, a new and improved method and apparatus for reconstructing an image representation of a region of interest of a subject including a radiation emitting source during a SPECT or nuclear camera scan is provided. A Compton camera detects and collects radiation data emitted from the subject as cone projection data. The cone projection data is converted into plane projection data which is reconstructed into an image representation.

In accordance with a more limited aspect of the present invention, line integrals are determined from the cone projection data where the line integrals are defined from a common vertex and along a surface of an associated cone integral. Plane integrals are then constructed based on the line integrals to obtain the plane projection data.

In accordance with a more limited aspect of the present invention, the line integrals are expanded by a spherical harmonic expansion.

In accordance with another aspect of the present invention, a diagnostic imaging system for reconstructing an image representation of a subject is provided. A plurality of radiation detectors are parallelly disposed to each other and detect radiation from an examination region. Electrical data is produced indicative of coordinate locations and energy values on each of the radiation detectors at which radiation is detected. The radiation detected is scattered by at least one of the radiation detectors at a scattering angle. A reconstruction processor reconstructs an image representation from the data collected. The diagnostic imaging system further includes a cone integral data processor which determines the scattering angle based on the energy values and the coordinate locations of the received radiation on the plurality of radiation detectors. The cone integral data processor generates cone integral data defined by (i) a vertex at a location where the radiation is detected on a first radiation detector of the plurality of radiation detectors nearest the examination region, and (ii) the scattering angle. A conversion processor converts the cone integral data to plane integral data which the reconstruction processor reconstructs into an image representation.

One advantage of the present invention is that image reconstruction is achievable from radiation data collected by a Compton camera.

Another advantage of the present invention is that mechanical collimators are eliminated from the diagnostic imaging system by the use of a Compton camera operating with electronic collimation.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
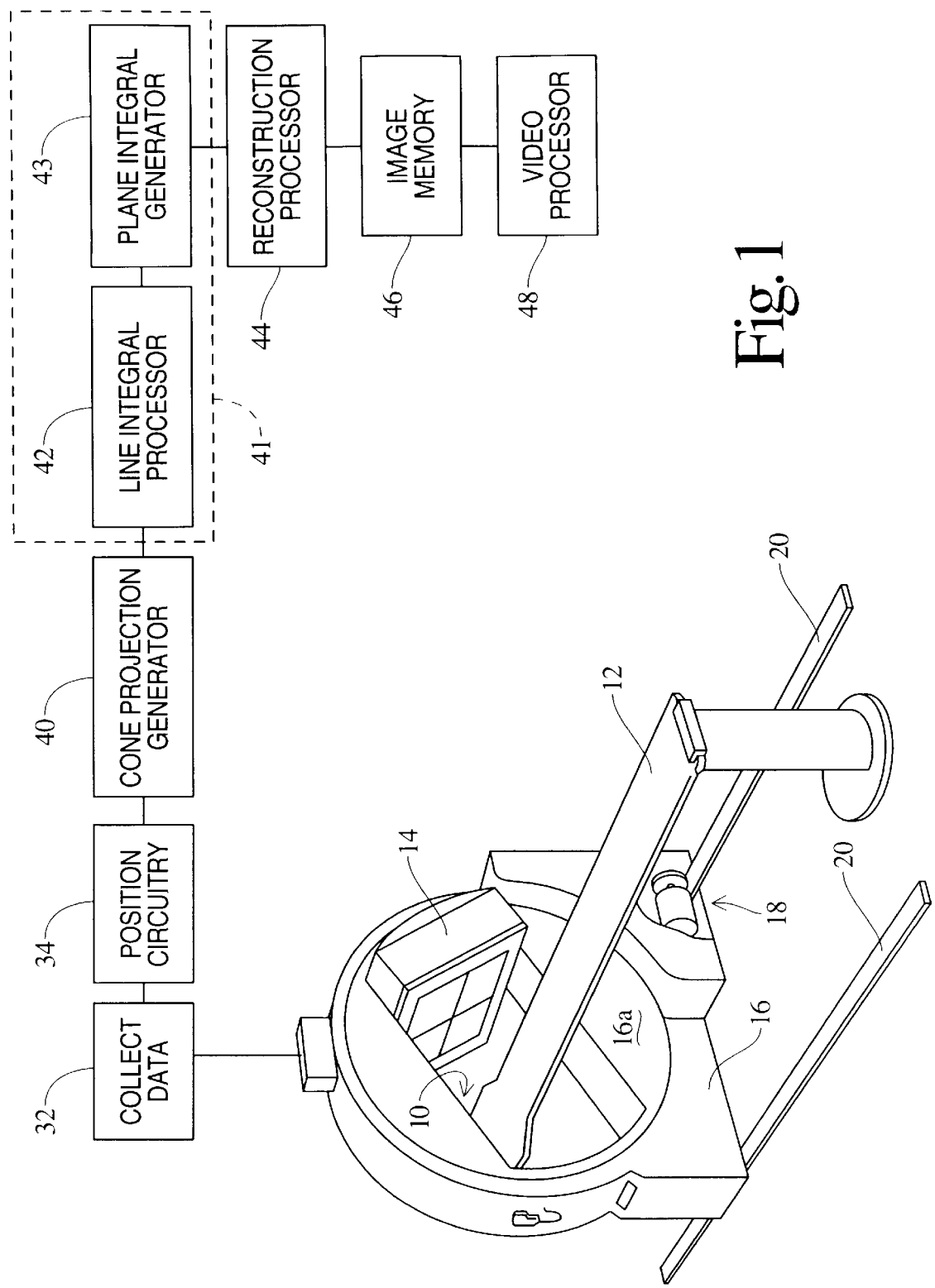
FIG. 1 is a diagrammatic illustration of a diagnostic imaging system in accordance with the present invention.

With reference to FIG. 1, a single photon emission computed tomography (SPECT) diagnostic imaging system has an examination region 10 for receiving a subject. A subject support or patient couch 12 adjustably positions the subject in the examination region 10. The examination region is viewed by a one-dimensional Compton camera 14 mounted on a gantry 16. It is to be appreciated that a greater number of cameras can be provided. The gantry includes a motor and drive assembly 18 which moves the gantry along tracks 20 so that selected regions of the subject may be imaged. The motor and drive assembly 18 also selectively rotates a rotatable portion 16a of the gantry and camera 14 around the subject such that selected views can be imaged by the camera 14.

Figure 2A:
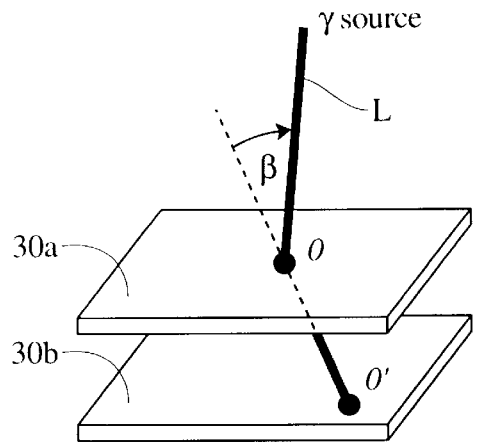
FIG. 2A is an illustration of a two detector Compton camera detecting an incident photon from a gamma source in accordance with the present invention.
Figure 2B:
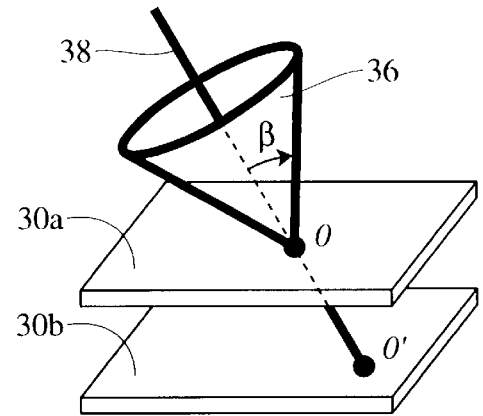
FIG. 2B illustrates a determination of a cone projection based on the detecting shown in FIG. 2A in accordance with the present invention.

With reference to FIGS. 2A and 2B, the Compton camera 14 is a two-dimensional camera which includes first and second radiation detectors or planes 30a and 30b disposed in parallel to each other and facing the examination region which contains a gamma source. For exemplary purposes, a photon emanating from the gamma source follows a path L and strikes the first detector 30a at a position O. The photon undergoes Compton scattering in the first detector 30a and is absorbed by the second detector 30b at a position O'. In other words, the path of the photon is changed or deflected by an angle β upon striking the first detector. This angle β is referred to as a scattering or Compton angle.

A data processor 32 collects the radiation data from the detectors 30a, 30b. Position and energy resolving circuitry 34 determines the detection positions O,O' and the energy values deposited by the photon at positions O,O'. An energy difference or energy loss ΔE during scattering is calculated based on the collected data. With the initial energy E and energy loss ΔE and using a Compton formula:

$$\cos\beta = 1 - \frac{mc^2 \Delta E}{(E-\Delta E)E}, \quad (1)$$

the scattering angle β is determined. Once the values of O,O' and β are known, a gamma source location of the photon is limited to be on a cone surface 36 which forms a vertex on the first detector 30a at position O and is defined by an angle from a central dividing line or axis 38 of the cone which is equal to the scattering angle β. For example as shown in FIG. 2B, the cone surface 36 defines an area in which possible locations of the gamma source reside.

A relationship between a three-dimensional gamma source distribution $f(\bar{x})$ and a rate of photon counting $q(O,O',\beta)$ for specific O,O' and β is given by $$q(O,O',\beta) \propto \int_{\text{cone}} f(\bar{x}) dA \quad (2)$$

where dA represents a unit area of a cone projection.

A cone projection data generator 40 generates cone projection data represented by the function $q(O,O',\beta)$. The cone projection data includes cone integrals which are defined by the measurements of energy deposited on the radiation detectors, the associated detection positions and scattering angle. At detection position O, a plurality of cone integrals are defined each based on a photon being detected. Since different photons typically have different energies and scattering angles, each of the cone integrals generally has a different orientation, a different aperture, and/or a different scattering angle from the other cone integrals. However, all the cone integrals for the detection position O are defined with a common vertex which is at position O. This process may be repeated for multiple positions on the front detector to generate cone integrals for each of the multiple positions.

Once cone projections are generated for a fixed location O on the front detector 30a, a conversion processor 41 converts the cone projections to plane projections. The conversion is performed by defining a relationship between the cone projections and equivalent plane projections for planes intersecting O. In the preferred embodiment, the plane projections are Radon projections. The conversion processor 41 includes a line integral processor 42 and a plane integral generator 43. The plane integral generator 43 generates Radon projections using the defined relationship for a given set of planes intersecting O from a corresponding set of cone projections. The generated planes are then summed. After generating a set of planes for a sufficient number of points O, a reconstruction processor 44 reconstructs the plane projections into an image representation of the subject which is stored in an image memory 46 and selectively displayed by a video processor 48. In the preferred embodiment, a filtered backprojection algorithm is used for reconstruction, for example three-dimensional Radon reconstruction. Of course, it is to be appreciated that any well-know image reconstruction method can be used to reconstruct the plane projections.

Figure 3A:
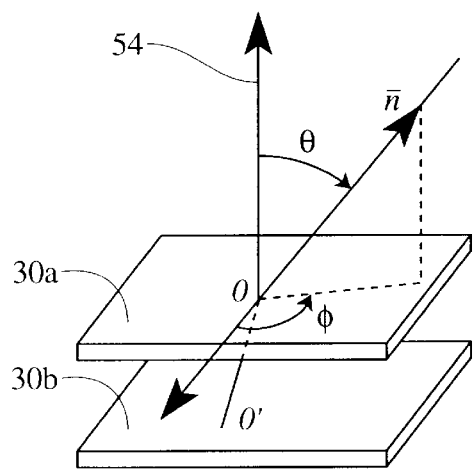
FIGS. 3A and 3B illustrate a relationship between a cone projection and associated unit vectors.
Figure 3B:
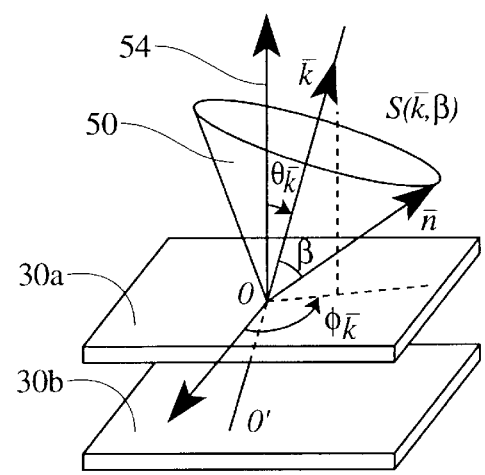

With reference to FIGS. 3A and 3B, for the fixed point O on the front detector 30a, two functions are defined where $q_{\bar{k}}(\beta)$ represents cone projections and $p(\bar{n})$ represents line integrals which define an associated cone projection as:

$$p(\bar{n}) \int_0^\infty f(O + \bar{n}r) r dr, \quad q_{\bar{k}}(\beta) = \int_{S(\bar{k},\beta)} p(\bar{n}) ds \quad (3)$$

where $\bar{k}$ is a unit vector along a center axis of a defined cone 50 having a vertex at position O and $\bar{n}$ is a unit vector along a surface of the defined cone 50 based on the scattering angle β. If vector $\bar{k}$ is in the direction O'O, then a cone projection $q_{\bar{k}}(\beta)$ is defined as:

$$q_{\bar{k}}(\beta) = \int_{\text{cone}} f(\bar{x}) dA \propto q(O,O',\beta). \quad (4)$$

Therefore $q_{\bar{k}}(\beta)$, as a function of both $\bar{k}$ and β, describes all cone projections associated with point O. It also follows from the definition of the cone projections $q_{\bar{k}}(\beta)$ that a Radon projection along a plane perpendicular to $\bar{k}$ and intersecting point O is equal to $q_{\bar{k}}(\pi/2)$. Thus, Radon projections are obtained from the cone projections.

With further reference to FIGS. 3A and 3B, the cone projection data (cone integrals) are represented by a set of unit vectors (line integrals) such as $\bar{n}$ which are defined along the surface of a cone integral. The line integral processor 42 generates the set of unit vectors defined by the function $p(\bar{n})$ whose values are initially unknown. The line integral processor 42 determines the unknown values of the unit vectors by forming a relationship between the unit vectors of the cone integral and the known measurement data of the cone integral, namely, the cone integral is equal to a sum of the unit vectors. Thus, the unknown values can be solved. Once the line integrals are determined, they form a basis for generating plane integrals which can be reconstructed into an image.

To further associate the cone integral and the line integrals, $p(\bar{n})$ is defined in spherical coordinates $(\theta,\phi)$ and can be expressed in terms of harmonic expansion as follows:

$$p(\theta,\phi) = \sum_{l=0}^{\infty} \sum_{m=-l}^{l} p_{lm} \cdot P_l^m(\cos\theta)e^{im\phi}. \tag{5}$$

The angle $\theta$ is measured from a line 54 normal to the detector 30a at point O.

A fundamental relationship between cone projections $q_{\bar{k}}(\beta)$ and expansion coeffients $p_{lm}$, is established as:

$$q_{\bar{k}}(\beta) = 2\pi\sin\beta \sum_{l=0}^{\infty} \left( \sum_{m=-l}^{l} p_{lm} \cdot P_l^m(\cos\theta_{\bar{k}})e^{im\phi_{\bar{k}}} \right) P_l^0(\cos\beta) \tag{6}$$

where $\theta_{\bar{k}}$ where $\phi_{\bar{k}}$ are spherical coordinates of a unit vector $\bar{k}$ shown in FIG. 3B. With this relationship, a Radon projection $q_{\bar{k}}(\pi/2)$ for any direction $\bar{k}$ can be obtained provided that expansion coefficients $p_{lm}$ are known. An exemplary method of determining the expansion coefficients $p_{lm}$ is to estimate them by a least square fitting of cone projections associated with point O into equation (6). Additionally, properties of Legandre polynomials as well as a fast Fourier transform can be used.

Figure 4:
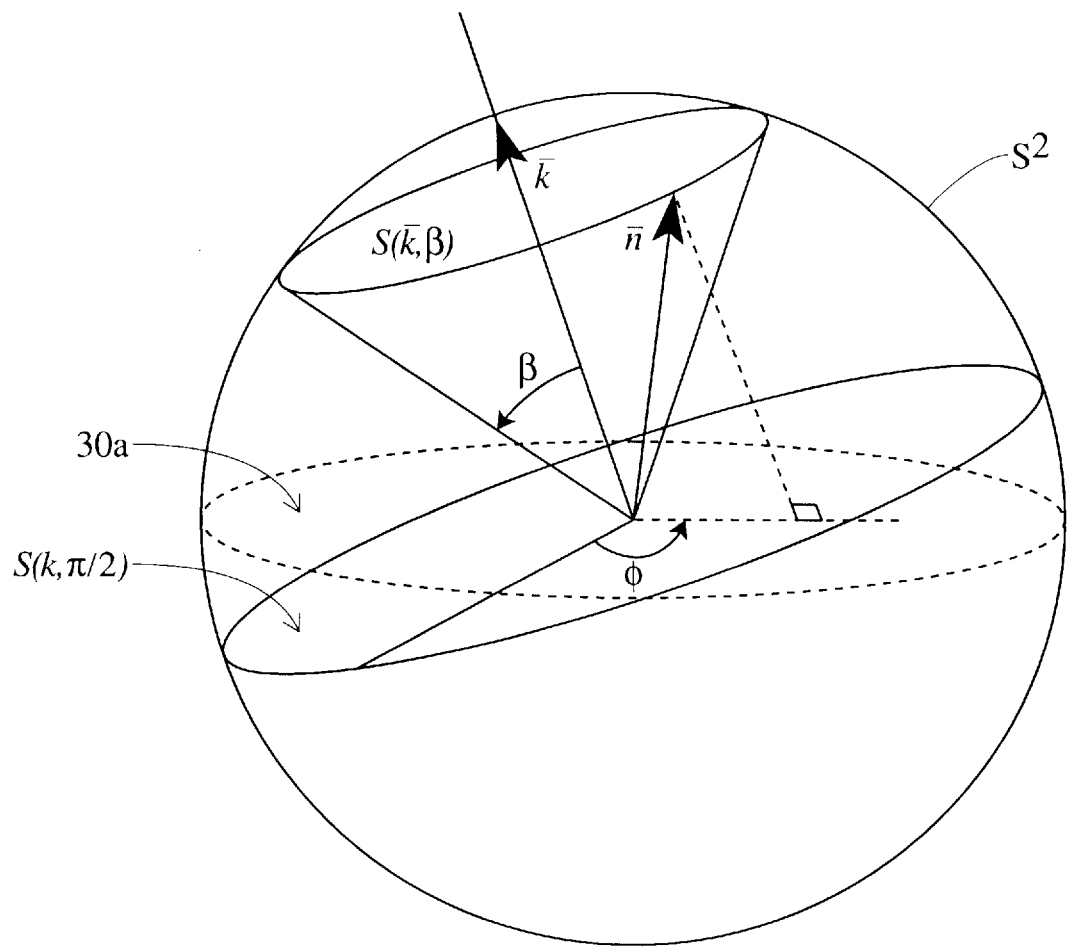
FIG. 4 illustrates a Radon projection plane generated from cone integral data and line integral data.

With reference to FIG. 4, the fundamental relationship of equation (6) is established. With any vector $\bar{k}$, spherical coordinates $(\theta,\phi)$ are associated with angle $\theta$ measured from $\bar{k}$, and a function $q_{\bar{k}}(\theta,\phi)$ is defined that represents $p(\bar{n})$ in the spherical coordinates $(\theta,\phi)$. Since both $\beta$ and $\theta$ are measured from the same direction $\bar{k}$, the cone projections $q_{\bar{k}}(\beta)$ are defined as:

$$q_{\bar{k}}(\beta) = \sin\beta \int_0^{2\pi} p_{\bar{k}}(\beta,\phi)d\phi. \tag{7}$$

Function $q_{\bar{k}}(\theta,\phi)$ is then expressed in terms of expansion in spherical harmonics as $$p_{\bar{k}}(\theta,\phi) = \sum_{l=0}^{\infty} \sum_{m=-l}^{l} p_{\bar{k}lm} \cdot P_l^m(\cos\theta)e^{im\phi} \tag{8}$$

which produces a relationship with equation (7) as:

$$q_{\bar{k}}(\beta) = 2\pi\sin\beta \sum_{l=0}^{\infty} P_{\bar{k}l0} \cdot P_l^0(\cos\beta). \tag{9}$$

The coordinate system is fixed corresponding to some vector $\bar{k}^o$, for example, where vector $\bar{k}^o$ is selected as being perpendicular to the detector plane 30a. The following notation is used:

$$p(\theta,\phi)=p_{\bar{k}^o}(\theta,\phi), \text{ where } p_{lm}=p_{\bar{k}^o,lm}. \tag{10}$$

Any unit vector $\bar{k}$ is uniquely represented in this coordinate system by two angles, $\theta_{\bar{k}},\phi_{\bar{k}}$, where $$p(\bar{k})=p_{\bar{k}}(\theta,\phi)=p(\theta_{\bar{k}},\phi_{\bar{k}}). \tag{11}$$

Equation (11) is then written in terms of Legandre expansion as $$\sum_{l=0}^{\infty} p_{\bar{k},l0} = \sum_{l=0}^{\infty} \sum_{m=-l}^{l} p_{lm} \cdot P_l^m(\cos\theta_{\bar{k}})e^{im\phi_{\bar{k}}}. \tag{12}$$

Since 2l+1 dimensional space of spherical harmonics $\{P_l^m(\cos\theta)e^{im\phi}, m=-1, \ldots, 1\}$ is invariant under rotations, it follows from equation (12) that for any l=0, $\ldots, \infty$ $$p_{\bar{k},l0} = \sum_{m=-l}^{l} p_{lm} \cdot P_l^m(\cos\theta_{\bar{k}})e^{im\phi_{\bar{k}}}. \tag{13}$$

Finally, combining this result with equation (9), the fundamental relationship between the cone projections $q_{\bar{k}}(\beta)$ and expansion coeffients $p_{lm}$ established in equation (6) is obtained as:

$$q_{\bar{k}}(\beta) = 2\pi\sin\beta \sum_{l=0}^{\infty} \left( \sum_{m=-l}^{l} p_{lm} \cdot P_l^m(\cos\theta_{\bar{k}})e^{im\phi_{\bar{k}}} \right) P_l^0(\cos\beta). \tag{14}$$

With further reference to FIG. 4, as established above, a set of cone projections associated with any fixed point O on the front detector 30a is described by the function $q_{\bar{k}}(\beta)$ defined on a three dimensional manifold $S^2 \times [0,\pi]$ where $S^2$ is a unit sphere. The function $p(\bar{n})$ defined on the unit sphere $S^2$ provides compact representation of the cone projection data $q_{\bar{k}}(\beta)$ as an integral along circle $S(\bar{k},\beta)$ with a center k and radius $\sin\beta$. Moreover, an integral of $p(\bar{n})$ along a great circle $S(\bar{k},\pi/2)$ is equal to a Radon projection along a plane perpendicular to $\bar{k}$. The great circle $S(\bar{k},\pi/2)$ is a circular plane within the unit sphere $S^2$ where $\beta=\pi/2$ and has a radius equal to the radius of the unit sphere $S^2$.

Figure 5:
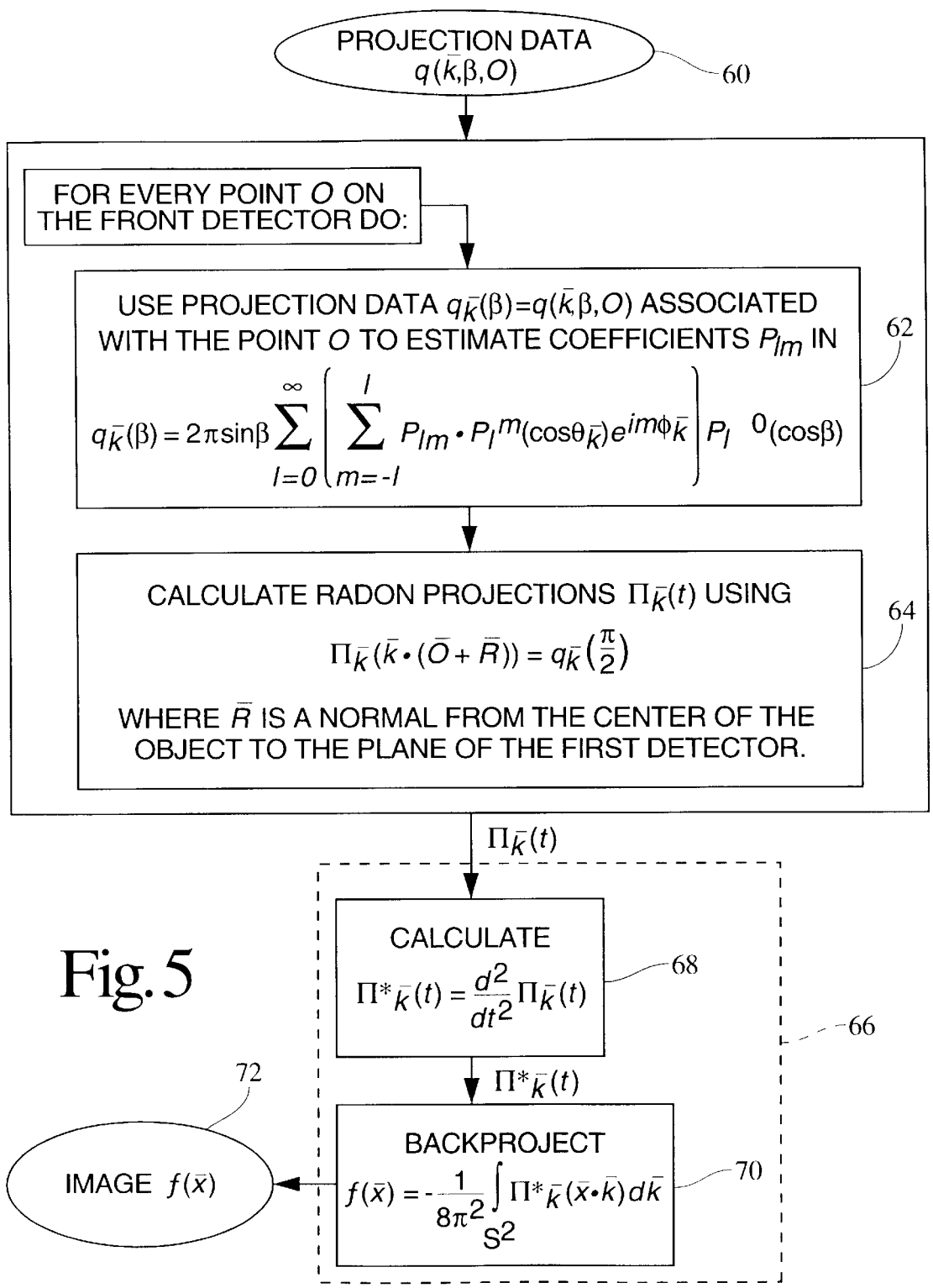
FIG. 5 is an example of an image reconstruction method in accordance with the present invention.
Figure 6:
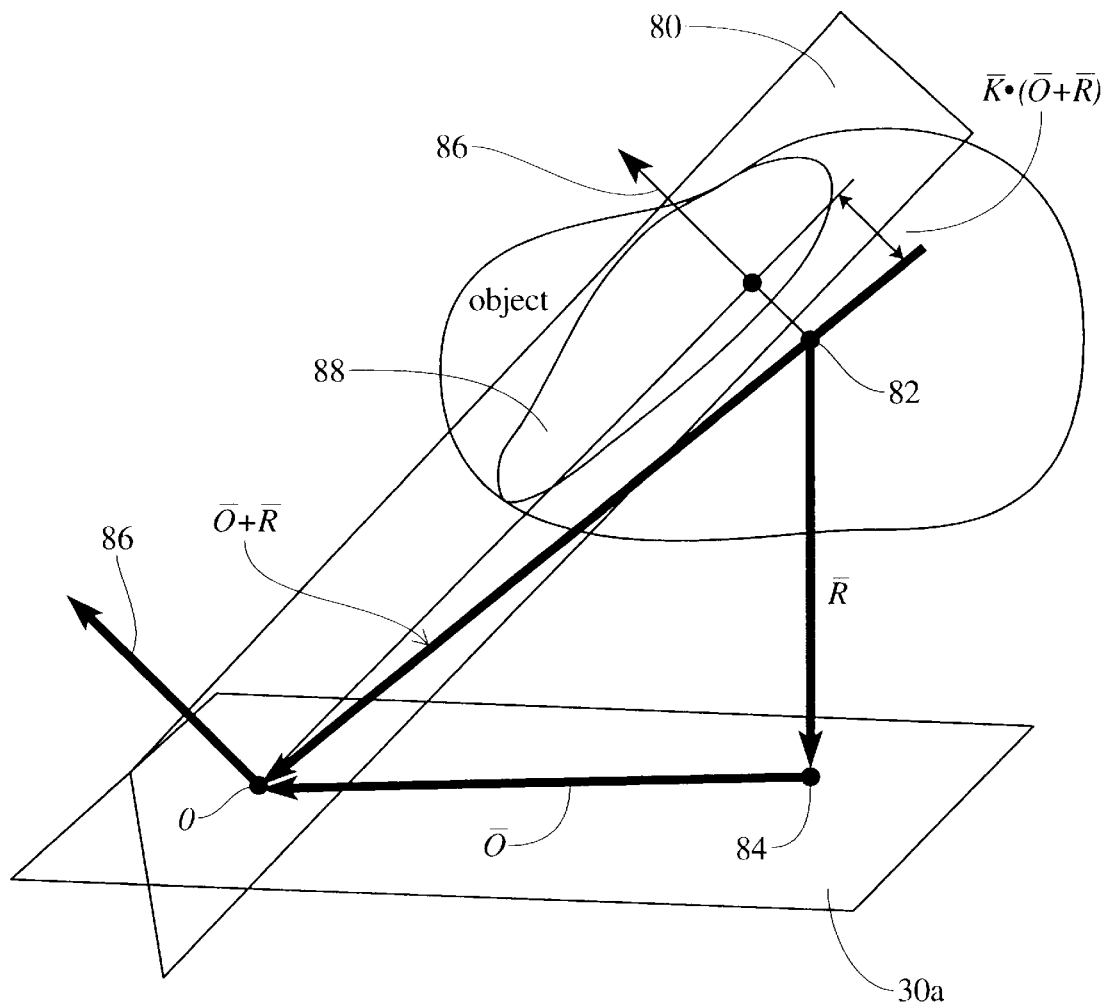
FIG. 6 is a graphical representation of a Radon integral plane found in accordance with the method of FIG. 5.

With reference to FIGS. 5 and 6, an exemplary image reconstruction is performed as follows:

Step 1. Radiation data is collected 60 from the detectors 30a, 30b. For every point O on the front detector 30a, cone projection data $q_{\bar{k}}(\beta)$ is generated 62 from radiation data collected by the detectors. Values of line integrals $p(\bar{n})$ are estimated from samples of the cone projection data $q_{\bar{k}}(\beta)$. The line integrals $p(\bar{n})$ are expanded in terms of spherical harmonics to assist in determining their values.

Step 2. Radon projections are calculated and formed 64 along planes intersecting point O from the estimated values of line integrals $p(\bar{n})$.

Step 3. The Radon projections are reconstructed 66 by filtering 68 and backprojecting 70 to generate an image 72.

With further reference to FIG. 6, an example of a radon projection or integral plane 80 generated by the foregoing method is shown. An object being imaged has a center or origin 82 and a normal $\bar{R}$ from the center 82 to the front detector 30a to a point 84 which represents the "origin" on the detector plane. With a photon being detected at point O which serves as a vertex of cone projection data, a vector is defined as $\bar{O}+\bar{R}$ from the object origin 82 towards the detection point O. A distance from the radon plane 80 to the object origin 82 is defined as $\bar{k}.(\bar{O}+\bar{R})$ and a normal 86 of the radon integral plane 80 is defined as $\bar{k}$. The formed radon plane 80 intersects the vertex O and defines a slice 88 through the object represented by the shaded region.

The present invention provides a new image reconstruction system and method for a Compton camera based on estimation of Radon projections followed by application of filtered backprojection. Using expansion in spherical harmonics allows efficient implementation of the reconstruction. A complete set of planar projections can be formed from only one camera position if the detector has infinite extent.

It is to be appreciated that the present invention finds application with telescopic systems which image distant objects based on energy distributions. An example includes a Compton telescope used in astronomy.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof

Having thus described the preferred embodiment, the invention is now claimed to be:

1. A method of generating an image representation of a region of interest of a subject by a diagnostic imaging system where the subject is injected with a radiation source, the method comprising:
   detecting a photon from the radiation source at a first position on a first radiation detection plane which scatters the photon at a scattering angle;
   detecting the scattered photon at a second position on a second radiation detection plane, the second radiation detector plane being parallel to the first radiation detection plane;
   defining cone integral data having a common vertex at the first position on the first radiation detection plane based on the scattering angle and energy deposited by the photon, a source of the photon lying along a surface represented by the cone integral data;
   generating line integral data which represents the cone integral data wherein a combined set of the line integral data being equivalent to a cone integral of the cone integral data;
   forming integral planes from the line integral data; and
   reconstructing the integral planes into an image representation of the region of interest of the subject.

2. The method of generating an image representation as set forth in claim 1 further including:
   defining the line integral data by a plurality of unit vectors defined by spherical coordinates;
   expanding the plurality of unit vectors based on spherical harmonic expansion to represent the cone integral data.

3. The method of generating an image representation as set forth in claim 1 wherein the integral planes include Radon integral planes.

4. The method of generating an image representation as set forth in claim 1 further including:
   detecting photons at a plurality of detection positions on the first radiation detection plane;
   defining a plurality of cone integral data for each of the plurality of detection positions; and
   repeating the steps of generating, forming and reconstructing for the plurality of cone integral data at each of the plurality of detection positions.

5. The method of generating an image representation as set forth in claim 1 wherein the integral planes formed each intersect the first position on the first radiation detection plane.

6. A diagnostic imaging system for reconstructing an image representation of a subject including a plurality of radiation detectors parallelly disposed to each other for detecting radiation from an examination region, and producing electrical data indicative of coordinate locations and energy values on each of the radiation detectors at which radiation is detected, the radiation detected being scattered by at least one of the radiation detectors at a scattering angle, and a reconstruction processor which reconstructs an image representation, the diagnostic imaging system comprising:
   a cone integral data processor for determining the scattering angle based on the energy values and the coordinate locations of the received radiation on the plurality of radiation detectors and generating cone integral data defined by (i) a vertex at a location where the radiation is detected on a first radiation detector of the plurality of radiation detectors nearest the examination region, and (ii) the scattering angle; and
   a conversion processor for converting the cone integral data to plane integral data which the reconstruction processor reconstructs into an image representation.

7. The diagnostic imaging system as set forth in claim 6 wherein the conversion processor includes a means for converting the cone integral data to plane integral data including spherical harmonic expansion.

8. The diagnostic imaging system as set forth in claim 6 wherein the conversion processor includes:
   a means for generating line integrals which represent the cone integral data; and
   a means for generating the plane integral data from the line integrals.

9. The diagnostic imaging system as set forth in claim 8 further including a means for applying spherical harmonic expansion to the line integrals to define a relationship between the line integrals and corresponding cone integral data.

10. The diagnostic imaging system as set forth in claim 6 wherein the plane integral data include Radon plane integrals.

11. The diagnostic imaging system as set forth in claim 6 wherein the conversion processor includes:
   a line integral processor for generating line integrals which represent the cone integral data; and
   a plane integral generator for generating the plane integral data from the line integrals.

12. A method of generating an image representation of a region of interest of a subject having radiation emitted therefrom, the radiation being detected by a Compton camera, the method comprising:
   collecting radiation data from the detected radiation as cone projection data;
   converting the cone projection data into plane projection data; and
   reconstructing an image representation from the plane projection data.

13. The method of generating an image representation as set forth in claim 12 further including:
   providing at least first and second radiation detectors for collecting the radiation data, the first radiation detector being disposed between the subject and the second radiation detector and being parallel to the second radiation detector, the detected radiation undergoing Compton scattering in the first radiation detector;
   determining detection positions of a photon detected on the first and second radiation detectors;
   determining an energy deposited by the photon on both the first and second radiation detectors at the detection positions; and determining the cone projection data based on the detection positions and the energy determined on both the first and second radiation detectors.

14. The method of generating an image representation as set forth in claim 13 wherein the cone projection data includes a plurality of cone integrals each having a common vertex, the common vertex being at the detection position on the first radiation detector.

15. The method of generating an image representation as set forth in claim 14 further including:

determining line integrals from each cone integral of the plurality of cone integrals, the line integrals being defined from the common vertex and along a surface of an associated cone integral; and constructing plane integrals based on the line integrals to obtain the plane projection data.

16. The method of generating an image representation as set forth in claim 15 wherein the determining includes defining the line integrals based on spherical coordinates and applying spherical harmonic expansion.

17. The method of generating an image representation as set forth in claim 12 wherein the converting includes:

determining line integrals which represent the cone projection data; and constructing plane integrals from selected groups of the line integrals to obtain the plane projection data.

18. The method of generating an image representation as set forth in claim 17 further including expanding the line integrals by spherical harmonic expansion to define an equivalency relationship with the cone projection data.

19. The method of generating an image representation as set forth in claim 12 wherein the plane projection data includes Radon plane projections and the reconstructing is three-dimensional Radon reconstruction.

20. The method of generating an image representation as set forth in claim 12 wherein the cone projection data includes a plurality of cone integrals each having a common vertex, the common vertex being at a common location at which radiation is detected.

* * * * *